US011006906B2

(12) United States Patent
Yano et al.

(10) Patent No.: US 11,006,906 B2
(45) Date of Patent: May 18, 2021

(54) ROBOTIC OPERATING TABLE, AND ROBOTIC OPERATING TABLE OPERATION DEVICE

(71) Applicants: MEDICAROID CORPORATION, Kobe (JP); SYSMEX CORPORATION, Kobe (JP)

(72) Inventors: Yutaro Yano, Kobe (JP); Yoshiyuki Tamura, Kobe (JP); Yukihiko Kitano, Kobe (JP); Toru Mizumoto, Kobe (JP); Kenichi Nakagawa, Kobe (JP); Yuuki Suzuki, Kyoto (JP); Hidetoshi Yoshioka, Takatsuki (JP); Yuko Hidaka, Osaka (JP); Yuichi Kageyama, Kyoto (JP)

(73) Assignees: MEDICAROID CORPORATION, Kobe (JP); SYSMEX CORPORATION, Kobe (JP)

( * ) Notice: Subject to any disclaimer, the term of this patent is extended or adjusted under 35 U.S.C. 154(b) by 409 days.

(21) Appl. No.: 15/906,112

(22) Filed: Feb. 27, 2018

(65) Prior Publication Data
US 2018/0242929 A1    Aug. 30, 2018

(30) Foreign Application Priority Data
Feb. 28, 2017    (JP) .............................. JP2017-035608

(51) Int. Cl.
*A61B 6/04*    (2006.01)
*A61G 13/06*    (2006.01)
(Continued)

(52) U.S. Cl.
CPC ............ *A61B 6/0487* (2020.08); *A61B 5/055* (2013.01); *A61B 6/0407* (2013.01);
(Continued)

(58) Field of Classification Search
USPC .................................................. 700/245–264
See application file for complete search history.

(56) References Cited

U.S. PATENT DOCUMENTS 5,778,467 A * 7/1998 Scott .................... A61G 13/009
5/612
6,302,579 B1 * 10/2001 Meyer .................. A61B 6/4429
378/195
(Continued)

FOREIGN PATENT DOCUMENTS

EP        1028684 B1    3/2004
JP    2008-539963 A    11/2008
(Continued)

OTHER PUBLICATIONS

The Japanese Office Action dated Feb. 19, 2019 in a counterpart Japanese patent application.
(Continued)

*Primary Examiner* — Jonathan L Sample
(74) *Attorney, Agent, or Firm* — Metrolex IP Law Group, PLLC

(57) ABSTRACT

A robotic operating table according to one or more embodiments may include: a patient placement table; a robotic arm comprising a plurality of joints, and having a first end supported on a base and a second end supporting the table; a light emitter provided to the table; and an operation device including a move operation unit that receives, from a user, a move operation to move the table. In one or more embodiments, while the move operation unit is receiving the move operation to move the table, the light emitter may emit light.

19 Claims, 6 Drawing Sheets

(51) Int. Cl.
*A61G 13/04* (2006.01)
*G08B 3/10* (2006.01)
*G08B 5/36* (2006.01)
*A61B 6/10* (2006.01)
*A61B 6/00* (2006.01)
*A61G 13/10* (2006.01)
*A61B 5/055* (2006.01)

(52) U.S. Cl.
CPC ............ *A61B 6/0442* (2013.01); *A61B 6/102* (2013.01); *A61B 6/105* (2013.01); *A61B 6/4441* (2013.01); *A61B 6/467* (2013.01); *A61B 6/54* (2013.01); *A61B 6/547* (2013.01); *A61B 6/548* (2013.01); *A61G 13/04* (2013.01); *A61G 13/06* (2013.01); *A61G 13/104* (2013.01); *G08B 3/10* (2013.01); *G08B 5/36* (2013.01); *A61G 2203/12* (2013.01); *A61G 2203/14* (2013.01); *A61G 2203/20* (2013.01); *A61G 2203/42* (2013.01); *A61G 2210/50* (2013.01)

(56) References Cited

U.S. PATENT DOCUMENTS

| | | | | |
|---|---|---|---|---|
| 6,351,678 B1* | 2/2002 | Borders | ............... | A61H 9/0078 700/83 |
| 6,566,833 B2* | 5/2003 | Bartlett | ................ | A61G 7/001 318/564 |
| 7,669,261 B2* | 3/2010 | Fruh | ...................... | A61G 13/08 5/616 |
| 7,860,550 B2* | 12/2010 | Saracen | ................ | A61B 6/548 600/410 |
| 8,126,114 B2* | 2/2012 | Naylor | ................... | A61B 34/71 378/65 |
| 8,160,205 B2* | 4/2012 | Saracen | ................ | A61N 5/1049 378/69 |
| 9,326,907 B2* | 5/2016 | Marle | ................... | A61B 6/4494 |
| 9,492,341 B2* | 11/2016 | Huster | ................ | A61G 7/0524 |
| 2003/0195644 A1* | 10/2003 | Borders | ............... | A61G 13/107 700/90 |
| 2005/0183023 A1* | 8/2005 | Maruyama | ............ | G06F 3/1423 715/759 |
| 2005/0228255 A1* | 10/2005 | Saracen | ................ | A61B 6/0487 600/407 |
| 2005/0234327 A1* | 10/2005 | Saracen | ................ | A61B 6/548 600/407 |
| 2008/0118035 A1* | 5/2008 | Maschke | .............. | A61B 6/0487 378/197 |
| 2008/0119714 A1* | 5/2008 | Meissner | ............. | A61B 6/4458 600/407 |
| 2008/0235872 A1* | 10/2008 | Newkirk | ................ | G06F 3/0481 5/600 |
| 2009/0274271 A1* | 11/2009 | Pfister | .................... | A61B 90/13 378/62 |
| 2010/0237257 A1* | 9/2010 | Saracen | ............... | A61N 5/1049 250/491.1 |
| 2010/0299014 A1* | 11/2010 | Bouvier | ............... | A61B 6/4405 701/25 |
| 2011/0004070 A1* | 1/2011 | Rist | ........................ | G16H 40/20 600/300 |
| 2011/0187875 A1* | 8/2011 | Sanchez | ................ | A61B 34/30 348/207.11 |
| 2012/0035462 A1* | 2/2012 | Maurer, Jr. | .......... | A61N 5/1077 600/411 |
| 2014/0229883 A1* | 8/2014 | Tsukijishin | .......... | A61B 6/4464 715/773 |
| 2015/0000038 A1* | 1/2015 | Obi | ........................ | A61G 13/02 5/601 |
| 2015/0201899 A1* | 7/2015 | Uchinomiya | .......... | G16H 30/20 378/62 |
| 2015/0257952 A1* | 9/2015 | Zerhusen | ............... | A61G 7/051 340/12.5 |
| 2015/0290806 A1* | 10/2015 | Garde | ....................... | H02P 3/16 700/245 |
| 2015/0317068 A1* | 11/2015 | Marka | .................. | G06F 3/04842 715/835 |
| 2016/0136814 A1* | 5/2016 | Garde | ...................... | B25J 13/00 700/264 |
| 2016/0354047 A1* | 12/2016 | Huston | ................. | A61B 6/5205 |
| 2017/0027533 A1* | 2/2017 | Sakaguchi | ............ | A61B 6/544 |
| 2017/0079722 A1* | 3/2017 | O'Grady | ................ | A61B 34/35 |
| 2017/0224298 A1* | 8/2017 | Hannemann | ........ | A61B 6/0492 |
| 2018/0147106 A1* | 5/2018 | Soundararajan | ....... | A61G 13/04 |
| 2018/0160994 A1* | 6/2018 | Harrington | .......... | A61N 5/1082 |

FOREIGN PATENT DOCUMENTS

| | | |
|---|---|---|
| JP | 2014-100301 A | 6/2014 |
| JP | 2016-054860 A | 4/2016 |
| WO | 2013/114737 A1 | 8/2013 |

OTHER PUBLICATIONS

The Office Action dated Jun. 30, 2020 in a counterpart Japanese patent application.

\* cited by examiner

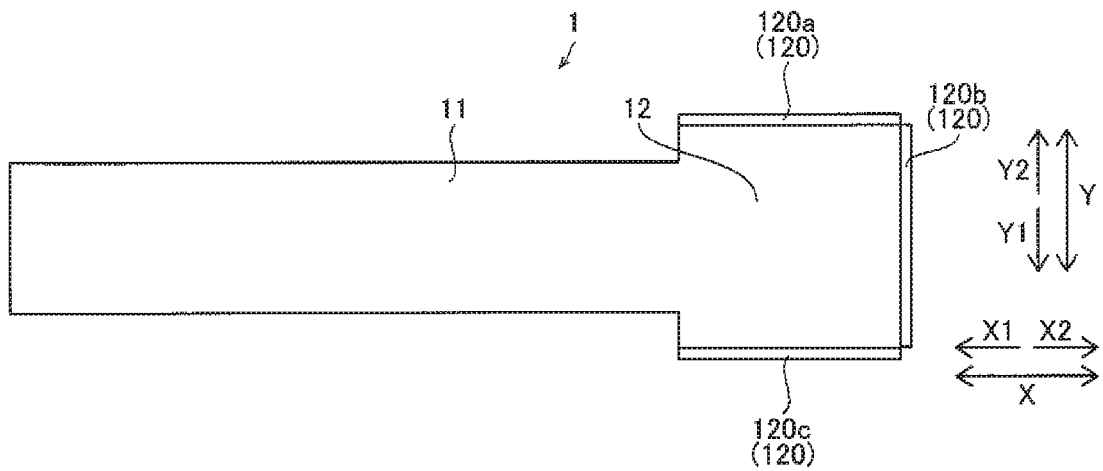
Fig. 4
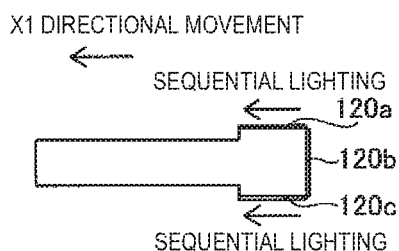
Fig. 5A
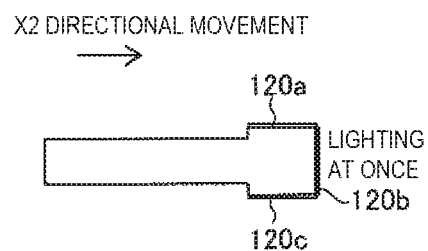
Fig. 5B
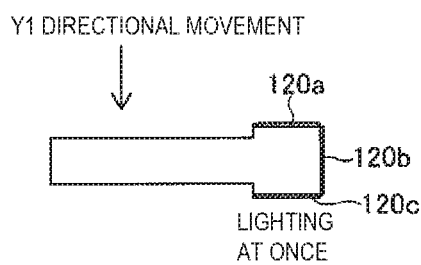
Fig. 5C
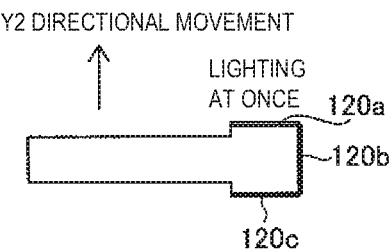
Fig. 5D
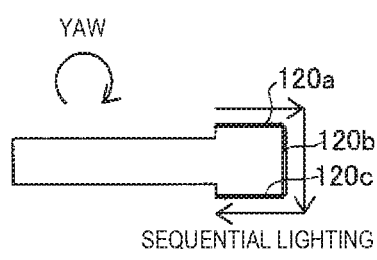
Fig. 5E
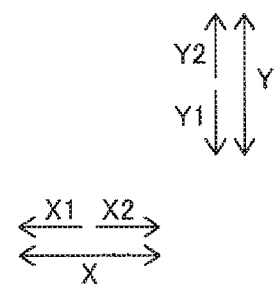

ROBOTIC OPERATING TABLE, AND ROBOTIC OPERATING TABLE OPERATION DEVICE

CROSS REFERENCE TO RELATED APPLICATIONS

This application claims priority to Japanese Patent Application No. 2017-035608 filed on Feb. 28, 2017, entitled "ROBOTIC OPERATING TABLE, AND ROBOTIC OPERATING TABLE OPERATION DEVICE", the entire contents of which is incorporated herein by reference.

BACKGROUND

One or more embodiments relate to a robotic operating table, a hybrid operation system, and a robotic operating table operation device.

Japanese Patent Application Publication No. 2014-100301 discloses a hybrid operation room including a combination of a radiographic fluoroscopic imaging apparatus and an operating table. The operating table of the hybrid operation room according to Japanese Patent Application Publication No. 2014-100301 slides a movable table in parallel to horizontal directions along a base fixed to the floor. The base is freely extendable and contractible in the vertical direction and is configured to raise and lower the table in the vertical direction.

SUMMARY

A robotic operating table according to one or more embodiments include: a patient placement table; a robotic arm comprising a plurality of joints, and having a first end supported on a base and a second end supporting the table; a light emitter provided to the table; and an operation device including a move operation unit that receives, from a user, a move operation to move the table. In one or more embodiments, while the move operation unit is receiving the move operation to move the table, the light emitter may emit light.

A robotic operating table according to one or more embodiments includes: a patient placement table; a robotic arm comprising a plurality of joints, and having a first end supported on a base and a second end supporting the table; a display; and an operation device including a move operation unit that receives, from a user, a move operation to move the table. In one or more embodiments, wherein the display may display a position of the table before movement and a position of the table after the movement in a distinguishable manner while the move operation unit is receiving the move operation to move the table.

A hybrid operation system according to one or more embodiments includes: a robotic operating table; and at least one of a radiographic imaging apparatus that captures a radiographic projection image of a patient and a magnetic resonance imaging apparatus that captures a magnetic resonance image of the patient. In one or more embodiments, the robotic operating table may include: a patient placement table; a robotic arm comprising a plurality of joints, and having a first end supported on a base and a second end supporting the table; a light emitter provided to the table; and an operation device including a move operation unit that receives, from a user, a move operation to move the table. In one or more embodiments, while the move operation unit is receiving the move operation to move the table, the light emitter may emit light.

A robotic operating table operation device according to one or more embodiments include: a display; and a move operation unit that receives, from a user, a move operation to move a patient placement table of the robotic operating table. In one or more embodiments, the operating table may include the table, and a robotic arm including a plurality of joints, and having a first end supported on a base and a second end supporting the table. In one or more embodiments, while the move operation unit is receiving the move operation to move the table, the display may display a position of the table before movement and a position of the table after the movement in a distinguishable manner.

BRIEF DESCRIPTION OF DRAWINGS

FIG. 4 is a plan view illustrating a light emitter of the robotic operating table according to one or more embodiments;

FIGS. 5A to 5E are diagrams illustrating examples of light emissions by the light emitter of the robotic operating table according to one or more embodiments;

DETAILED DESCRIPTION

Figure 1:
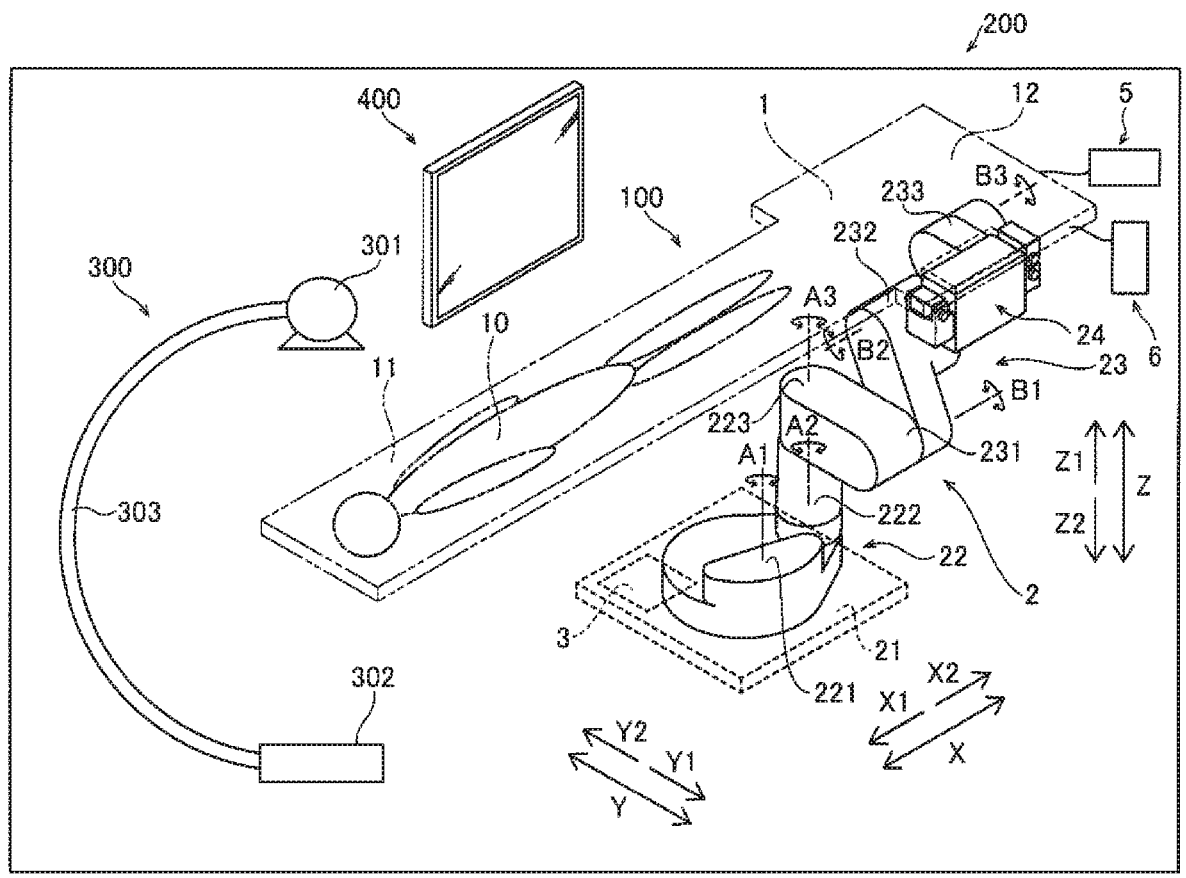
FIG. 1 is a diagram schematically illustrating a hybrid operation room including a robotic operating table according to one or more embodiments.

One or more embodiments are described with reference to drawings, in which the same constituents are designated by the same reference numerals and duplicate explanation concerning the same constituents may be omitted for brevity and ease of explanation. The drawings are illustrative and exemplary in nature and provided to facilitate understanding of the illustrated embodiments and may not be exhaustive or limiting. Dimensions or proportions in the drawings may not be to scale, and are not intended to impose restrictions on the disclosed embodiments. For this reason, specific dimensions and the like should be interpreted with the accompanying descriptions taken into consideration. In addition, the drawings may include parts whose dimensional relationship and ratios are different from one drawing to another.

Prepositions, such as "on", "over" and "above" may be defined with respect to a surface, for example a layer surface, regardless of the orientation of the surface in space.

(Configuration of Operating Table)

The following describes the configuration of a robotic operating table 100 according to one or more embodiments with reference to FIGS. 1 to 8.

As illustrated in FIG. 1, the robotic operating table 100 is provided in a hybrid operation room 200. The hybrid operation room 200 is provided with a radiographic imaging apparatus 300 that captures a radiographic projection image of a patient 10. The hybrid operation room 200 may also be provided with a display 400 for displaying information on a surgical operation. In other words, the hybrid operation room 200 may be provided with a hybrid operation system 201 including the robotic operating table 100 and the radiographic imaging apparatus 300. The display 400 may be suspended by, for example, an arm (not illustrated) and may be movable inside the hybrid operation room 200. The robotic operating table 100 is used as a table for a surgical operation performed in, for example, surgery or internal medicine. The robotic operating table 100 is capable of moving a table 1 to a placement position at which to place the patient 10 onto the table 1, and moving the patient 10 to, for example, a patient receiving position, an anesthetization position, a surgical operation position, a test position, a treatment position, a radiographic imaging position, and a patient passing position while the patient 10 is placed on the table 1. The robotic operating table 100 is also capable of tilting the patient 10 while the patient 10 is placed on the table 1.

Figure 3:
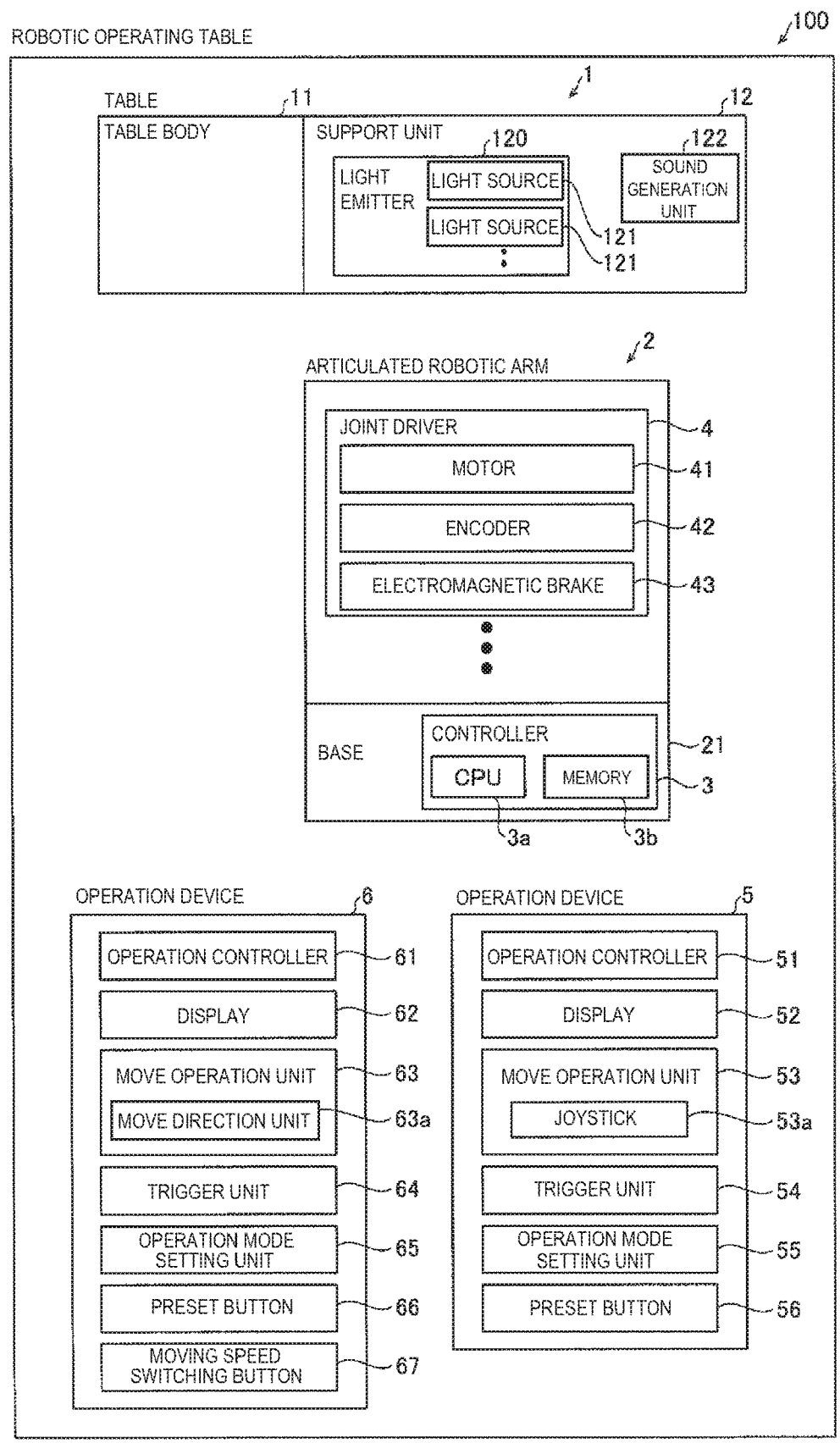
FIG. 3 is a block diagram illustrating a robotic operating table according to one or more embodiments.

The robotic operating table 100 includes the patient placement table 1, a robotic arm 2, a controller 3, an operation device 5, and an operation device 6. The robotic arm 2 may be an articulated robotic arm, which includes a plurality of joints. The table 1 includes a table body 11 and a support unit 12 supporting the table body 11. As illustrated in FIG. 3, the table 1 also includes a light emitter 120, and a sound generation unit 122. As illustrated in FIG. 1, the robotic arm 2 includes a base 21, a horizontal articulated assembly 22, a vertical articulated assembly 23, and a pitch mechanism 24. The horizontal articulated assembly 22 includes horizontal joints 221, 222 and 223. The vertical articulated assembly 23 includes vertical joints 231, 232 and 233. The radiographic imaging apparatus 300 includes an X-ray irradiation unit 301, an X-ray detection unit 302, and a C-arm 303. The operation devices 5 and 6 are each an exemplary "robotic operating table operation device" in the claims. The horizontal joints 221 to 223 and the vertical joints 231 to 233 may be examples of "joint" in one or more recited embodiments.

Figure 2:
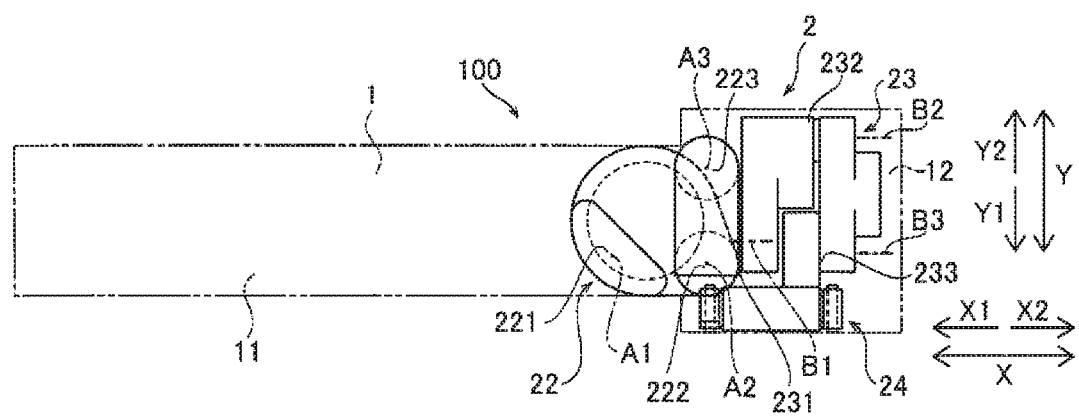
FIG. 2 is a plan view illustrating a robotic operating table according to one or more embodiments.

As illustrated in FIGS. 1 and 2, the table 1 has a substantially rectangular flat plate shape. The table 1 has a substantially flat upper surface. The longitudinal direction of the table 1 is aligned with an X direction, and the transverse direction of the table 1 is aligned with a Y direction. The table 1 may be rotatable about an axis extending in a vertical direction (Z direction). In this example, the X direction is defined to be a horizontal direction along the longitudinal direction of the table 1, and the Y direction is defined to be a horizontal direction along the transverse direction of the table 1. Thus, the X direction and the Y direction are directions with reference to the table 1.

As illustrated in FIG. 1, the patient 10 is placed onto the table body 11 of the table 1. The table body 11 is disposed on an X1 direction side of the table 1. The table body 11 has a substantially rectangular shape. The table body 11 may be made of an X-ray transmittable material. The table body 11 may be made of, for example, a carbon material (graphite). The table body 11 may be made of, for example, carbon fiber reinforcement plastic (CFRP). With this configuration, a radiographic image of the patient 10 may be captured while the patient 10 is placed on the table body 11.

The support unit 12 of the table 1 is connected with the robotic arm 2. The support unit 12 is disposed on an X2 direction side of the table 1. The support unit 12 has a substantially rectangular shape. The support unit 12 supports the table body 11. The support unit 12 may be made of a material having an X-ray transmissivity smaller than that of the table body 11. The support unit 12 may be made of, for example, metal. The support unit 12 may be made of, for example, a steel material or an aluminum material.

The table 1 is moved by the robotic arm 2. Specifically, the table 1 is movable in the X direction along a horizontal direction, the Y direction along a horizontal direction orthogonal to the X direction, and the Z direction along a vertical direction orthogonal to the X direction and the Y direction. The table 1 may freely rotate (roll) about an axis extending in the X direction. The table 1 may also freely rotate (pitch) about an axis extending in the Y direction. The table 1 may also freely rotate (yaw) about an axis extending in the Z direction.

The light emitter 120 emits light to notify movement of the table 1. As illustrated in FIG. 3, the light emitter 120 includes light sources 121. Each light source 121 is, for example, a light-emitting diode. Light emitters 120 are disposed at the support unit 12 of the table 1. Specifically, as illustrated in FIG. 4, the light emitters 120 are provided on side surfaces of the support unit 12. Thus, the light emitters 120 are provided near one end of the table 1 in the longitudinal direction (X direction). Specifically, light emitters 120 are provided on side parts on both sides (Y1 direction side and Y2 direction side) of the table 1 in the transverse direction (Y direction), and a light emitter 120 is provided on a side part of the table 1 on the X2 direction side. In other words, the light emitters 120 are disposed in a substantially C shape in plan view. The light emitters 120 include a light emitter 120a provided on the side part on the Y2 direction side, a light emitter 120b provided on the side part on the X2 direction side, and a light emitter 120c provided on the side part on the Y1 direction side. The light sources 121 of each light emitter 120 sequentially emit light in accordance with the moving direction of the table 1.

The sound generation unit 122 generates notification sound to notify movement of the table 1. Specifically, the sound generation unit 122 generates notification electronic sound and a notification sound message. The sound generation unit 122 includes a speaker. The sound generation unit 122 generates the notification sound under control of the controller 3.

The robotic arm 2 moves the table 1. As illustrated in FIG. 1, the robotic arm 2 has one end supported on the base 21 fixed to the floor, and the opposite end supporting the table 1. Specifically, the robotic arm 2 is supported on the base 21 to be rotatable about a base rotation axis (rotation axis A1) substantially perpendicular to an installation surface on which the base 21 is installed. The robotic arm 2 supports the vicinity of one end of the table 1 on the X2 direction side in the longitudinal direction (X direction). In other words, the opposite end of the robotic arm 2 supports the support unit 12 at the vicinity of the one end of the table 1.

The robotic arm 2 is capable of moving the table 1 with seven degrees of freedom. Specifically, the horizontal articulated assembly 22 provides the robotic arm 2 with three degrees of freedom to rotate about the rotation axis A1 extending in the vertical direction, rotate about a rotation axis A2 extending in the vertical direction, and rotate about a rotation axis A3 extending in the vertical direction. In addition, the vertical articulated assembly 23 provides the robotic arm 2 with three degrees of freedom to rotate about a rotation axis B1 extending in the horizontal direction, to rotate about a rotation axis B2 extending in the horizontal direction, and to rotate about a rotation axis B3 extending in the horizontal direction. In addition, the pitch mechanism 24 provides the robotic arm 2 with one degree of freedom to pitch the table 1 about a rotation axis extending in the transverse direction (Y direction).

The base 21 is buried and fixed in the floor. The base 21 is provided substantially at the center of a movement range of the table 1 in plain view (when viewed in the Z direction).

As illustrated in FIG. 3, the horizontal joints 221 to 223 and the vertical joints 231 to 233 are each provided with a joint driver 4. The horizontal joints 221 to 223 and the vertical joints 231 to 233 are each driven by the joint driver 4 thus provided. The joint driver 4 includes a motor 41, an encoder 42, an electromagnetic brake 43, and a decelerator (not illustrated). The horizontal joints 221 to 223 and the vertical joints 231 to 233 are each rotated about a rotation axis through drive of the motor 41.

The motor 41 includes a servomotor. The motor 41 is driven under control of the controller 3. The electromagnetic brake 43 brakes a joint (the horizontal joints 221 to 223 and the vertical joints 231 to 233). The encoder 42 senses a drive amount of the motor 41 and transmits a result of the sensing to the controller 3. The electromagnetic brake 43 is a non-excitation actuation electromagnetic brake that brakes the motor 41 when the motor 41 is not energized. The electromagnetic brake 43 may be a built-in electromagnetic brake of the motor 41 or an electromagnetic brake externally connected with the motor 41.

As illustrated in FIG. 2, the robotic arm 2 is disposed entirely behind the table 1 in plan view (when viewed in the Z direction). For example, the robotic arm 2 is housed in a housing space below the table 1 when the table 1 is positioned at the surgical operation position. Specifically, the robotic arm 2 is folded completely behind the table 1 in plan view (when viewed in the Z direction) when the table 1 is moved to a position for a surgical operation or treatment on the patient 10 being placed on the table 1. When the robotic arm 2 is folded, the length of the robotic arm 2 in a direction parallel to the longitudinal direction of the table 1 is shorter than half of the length of the table 1 in the longitudinal direction.

The robotic arm 2 causes the table 1 to yaw about an axis extending in the vertical direction (Z direction) by using at least one horizontal joint (at least one of the joints 221, 222, and 223). The robotic arm 2 causes the table 1 to roll about an axis extending in the longitudinal direction (X direction) by using at least one vertical joint (at least one of the joints 231, 232, and 233). The robotic arm 2 causes the table 1 to pitch about an axis extending in the transverse direction (Y direction) by using the pitch mechanism 24.

The controller 3 is a control circuit including, for example, a central processing unit (CPU) 3a, and a memory 3b. The memory 3b according to one or more embodiments may include such devices as a flash memory device, magnetic disk device such as a hard disk drive, and an optical disk device that reads data from a recording medium. In one or more embodiments, for example, the recording medium may include Blu-ray disk, CD-ROM (Compact Disk Read Only Memory), DVD (Digital Versatile Disk). The controller 3 is installed in the base 21 and controls movement of the table 1 by the robotic arm 2. Specifically, the controller 3 controls drive of the robotic arm 2 to move the table 1 based on an operation by a medical person (operator). The controller 3 acquires the posture of the robotic arm 2 and the position and posture of the table 1 based on an output from the encoder 42 of the motor 41 of each joint.

The operation devices 5 and 6 each receive an operation to move the table 1 by the medical person (operator). The operation devices 5 and 6 are each capable of performing an operation of the table 1. The operation device 5 is attached to the table 1 and used. The operation device 6 may be disposed at a position separate from the table 1. The operation devices 5 and 6 are attached to the table 1 through engagement members provided on side surfaces of the support unit 12 of the table 1. The operation devices 5 and 6 are connected with the controller 3 through wired communication.

Figure 7:
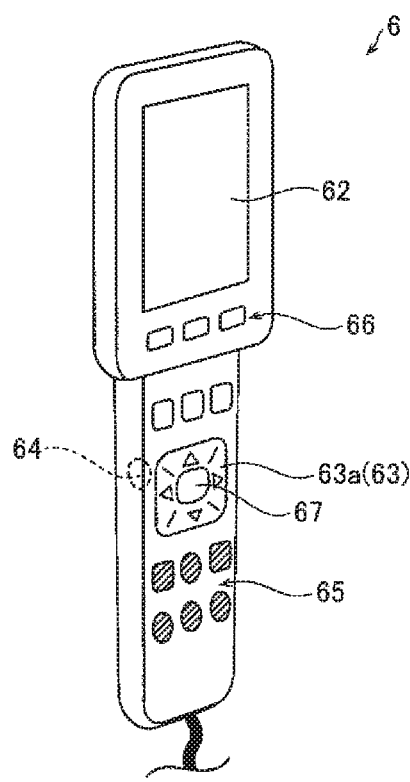
FIG. 7 is a perspective view illustrating an operation device of the robotic operating table including a move direction unit according to one or more embodiments.

As illustrated in FIGS. 3 and 5, the operation device 5 includes an operation controller 51, a display 52, a move operation unit 53 including a joystick 53a, a trigger unit 54, an operation mode setting unit 55, a preset button 56, and a moving speed switching button 57. As illustrated in FIGS. 3 and 7, the operation device 6 includes an operation controller 61, a display 62, the move operation unit 63 including move direction units 63a, a trigger unit 64, an operation mode setting unit 65, a preset button 66, and a moving speed switching button 67.

In one or more embodiments, while the move operation unit 53 or 63 is receiving a move operation to move the table 1, the controller 3 may control the light emitters 120 to emit light. In addition, while the move operation unit 53 or 63 is receiving a move operation to move the table 1, the controller 3 controls the sound generation unit 122 to generate notification sound. Specifically, when the table 1 is moved, the controller 3 controls the sound generation unit 122 to generate electronic sound. When the table 1 is moved to a registered preset position in advance, the controller 3 notifies the movement to the preset position by sound. For example, the patient receiving position, the anesthetization position, the surgical operation position, the test position, the treatment position, the X-ray imaging position, and the patient passing position are registered as preset positions. The preset positions are registered separately for each operative procedure of a surgical operation. Position information of the table 1 at a registered preset position and posture information of the robotic arm 2 at that time are stored in the memory 3b of the controller 3.

In one or more embodiments, while the move operation unit 53 or 63 is receiving a move operation to move the table 1 in a predetermined direct one or more embodiments ion, the controller 3 controls the light sources 121 to emit light to indicate that the table 1 is moving in the predetermined direction. In addition, while the move operation unit 53 or 63 is receiving a move operation to rotate the table 1 in a predetermined direction in a horizontal plane, the controller 3 controls the light sources 121 to sequentially emit light to indicate that the table 1 is rotating in the predetermined direction. Specifically, as illustrated in FIGS. 5A to 5E, the controller 3 controls the light sources 121 of each light emitter 120 to emit light in accordance with the moving direction.

For example, as illustrated in FIG. 5A, when the table 1 is moved in the X1 direction, the controller 3 turns on the light sources 121 of the light emitters 120a and 120c sequentially toward the X1 direction. In this case, the light emitter 120b is not turned on. As illustrated in FIG. 5B, when the table 1 is moved in the X2 direction, the controller 3 turns on the light sources 121 of the light emitter 120b at once. In this case, the light emitters 120a and 120c are not turned on.

As illustrated in FIG. 5C, when the table 1 is moved in the Y1 direction, the controller 3 turns on the light sources 121 of the light emitter 120c at once. In this case, the light emitters 120a and 120b are not turned on. As illustrated in FIG. 5D, when the table 1 is moved in the Y2 direction, the controller 3 turns on the light sources 121 of the light emitter 120a at once. In this case, the light emitters 120b and 120c are not turned on. As illustrated in FIG. 5E, when the table 1 is caused to yaw about an axis extending in the vertical direction (Z direction), the controller 3 turns on the light sources 121 of the light emitters 120a to 120c sequentially along the direction of rotation.

The controller 3 controls drive of the robotic arm 2 to move the table 1 while at least one of the move direction units 63a is operated. Accordingly, if the operation device 6 is enabled to receive an operation by a medical person (operator), the table 1 is moved only while at least one of the move direction units 63a is operated.

The controller 3 controls drive of the robotic arm 2 to move the table 1 while the joystick 53a is operated. Accordingly, if the operation device 5 is enabled to receive an operation by a medical person (operator), the table 1 is moved only while the joystick 53a is operated.

The controller 3 controls drive of the robotic arm 2 to move the table 1 while the trigger unit 54 (64) and the move operation unit 53 (63) are operated together. Accordingly, if the operation device 5 is enabled to receive an operation by a medical person (operator), the table 1 is moved only while the operation of pressing the trigger unit 54 and the operation of tilting the joystick 53a are performed together. If the operation device 6 is enabled to receive an operation by a medical person (operator), the table 1 is moved only while the operation of pressing the trigger unit 64 and the operation of pressing one of the move direction units 63a are performed together. When an operator stops the operation of the move operation unit 53 (63) with the trigger unit 54 (64) operated, the controller 3 stops the movement of the table 1 and the notification sound by the sound generation unit 122, and controls the light emitters 120 to emit light in a color different from that during the movement. When the operator stops the operation of the trigger unit 54 (64), the controller 3 controls the light emitters 120 to stop light emission.

The operation controller 51 (61) controls each component of the operation device 5 (6) based on an operation by the medical person (operator). Specifically, the operation controller 51 (61) controls the display 52 (62) to display an image based on an operation by the medical person (operator). The operation controller 51 (61) transmits operation information to the controller 3 based on an operation by the medical person (operator).

The display 52 (62) displays, for example, the state of the table 1, the state of an operation of the operation device 5 (6), and an operation screen. The display 52 (62) includes a liquid crystal display or an organic electroluminescence (EL) display. In the hybrid operation room 200, the controller 3 of the robotic operating table 100, the operation controller 51 (61) of the operation device 5 (6), and the display 400 (refer to FIG. 1) are connected with each other to perform communication therebetween. The display 400 is capable of displaying, for example, the state of the table 1, the state of an operation of the operation device 5 (6), and the operation screen. The display 400 is capable of displaying, for example, an image displayed by the display 52 (62) of the operation device 5 (6). With this configuration, in the hybrid operation room 200, the operation state of the robotic operating table 100 may be checked by medical persons all at once. The display 400 may be an inputting and display including a touch panel to receive, from a medical person (user) through an operation on a screen, an operation to move the table 1.

The move operation unit 53 (63) receives, from a user (medical person), a move operation to move the table 1. The move operation unit 53 of the operation device 5 includes the joystick 53a. The joystick 53a is operated by being tilted. The joystick 53a receives an operation to move the table 1 in accordance with the direction and angle of the tilt. The move operation unit 63 of the operation device 6 includes the move direction units 63a for respective directions in which the table 1 is moved. The move direction units 63a are provided for eight directions, for example. Each move direction units 63a is receives an operation to move the table 1 by being pressed.

The trigger unit 54 (64) is provided to enable the operation of the move-operation unit 53 (63). Specifically, energization of the motor 41 is turned on when the trigger unit 54 (64) is operated. With this configuration, braking of the motor 41 by the electromagnetic brake 43 is released by operating the trigger unit 54 (64). As a result, only while the trigger unit 54 (64) is operated, the operation of the move operation unit 53 (63) is enabled, so that the table 1 can be moved. In the robotic operating table 100, energization of the motor 41 is turned off when the operation of the trigger unit 54 (64) is released. With this configuration, the motor 41 is braked by the electromagnetic brake 43 by releasing the operation of the trigger unit 54 (64). As a result, when the trigger unit 54 (64) is not operated, the operation of the move operation unit 53 (63) is disabled, so that the table 1 cannot be moved.

The trigger unit 54 of the operation device 5 is provided at a leading end of the joystick 53a. In the operation device 5, the operation of the joystick 53a is enabled when the trigger unit 54 is pressed. The operation of the joystick 53a is disabled while the pressing on the trigger unit 54 is released. The trigger unit 64 of the operation device 6 is provided on a surface opposite to a surface on which the move direction units 63a are provided. In the operation device 6, the operation of the move direction units 63a is enabled when the trigger unit 64 is pressed. The operation of the move direction units 63a is disabled while the pressing on the trigger unit 64 is released.

The operation mode setting unit 55 (65) is provided to set one of operation modes. The operation modes include a yaw mode in which the table 1 is rotated about a rotation axis extending in the vertical direction (Z direction) in a horizontal plane, a horizontal movement mode in which the table 1 is linearly moved in a horizontal plane, a vertical movement mode in which the table 1 is vertically moved, a roll mode in which the table 1 is rotated about an axis parallel to the longitudinal direction (X direction) of the table 1, and a pitch mode in which the table 1 is rotated about an axis parallel to the transverse direction (Y direction) of the table 1. In the yaw mode, the table 1 is caused to yaw in accordance with an operation. In the horizontal movement mode, the table 1 is moved in the horizontal direction in accordance with an operation. In the vertical movement mode, the table 1 is moved in the vertical direction (Z direction) in accordance with an operation. In the roll mode, the table 1 is caused to roll in accordance with an operation. In the pitch mode, the table 1 is caused to pitch in accordance with an operation. The table 1 is moved when the trigger unit 54 (64) and the move operation unit 53 (63) are operated with an operation mode selected by the operation mode setting unit 55 (65).

Figure 6:
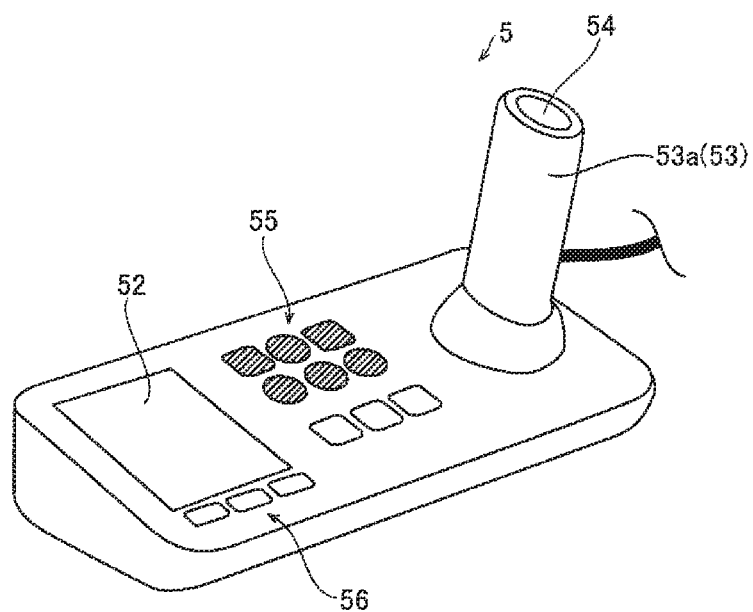
FIG. 6 is a perspective view illustrating an operation device of the robotic operating table including a joystick according one or more embodiments.

As illustrated in FIG. 6 (FIG. 7), the operation mode setting unit 55 (65) and the move operation unit 53 (63) have background colors different from each other. In other words, the operation mode setting unit 55 (65) and the move operation unit 53 (63) are distinguishable from each other by color tone.

The preset button 56 (66) is provided to set a movement destination of the table 1 as a preset position and register the current position of the table 1 as a preset position. When the current position of the table 1 is registered as a preset position by the preset button 56 (66), position information of the table 1 and posture information of the robotic arm 2 at that time are stored in the memory 3b of the controller 3. When the trigger unit 54 (64) and the move operation unit 53 (63) are operated while a preset position is selected by the preset button 56 (66), the table 1 is moved to the selected preset position.

The moving speed switching button 67 is provided to change the moving speed of the table 1. The moving speed of the table 1 is switched at stages at each press on the moving speed switching button 67. For example, the moving speed of the table 1 is switchable between moving speeds at three stages.

Figure 8:
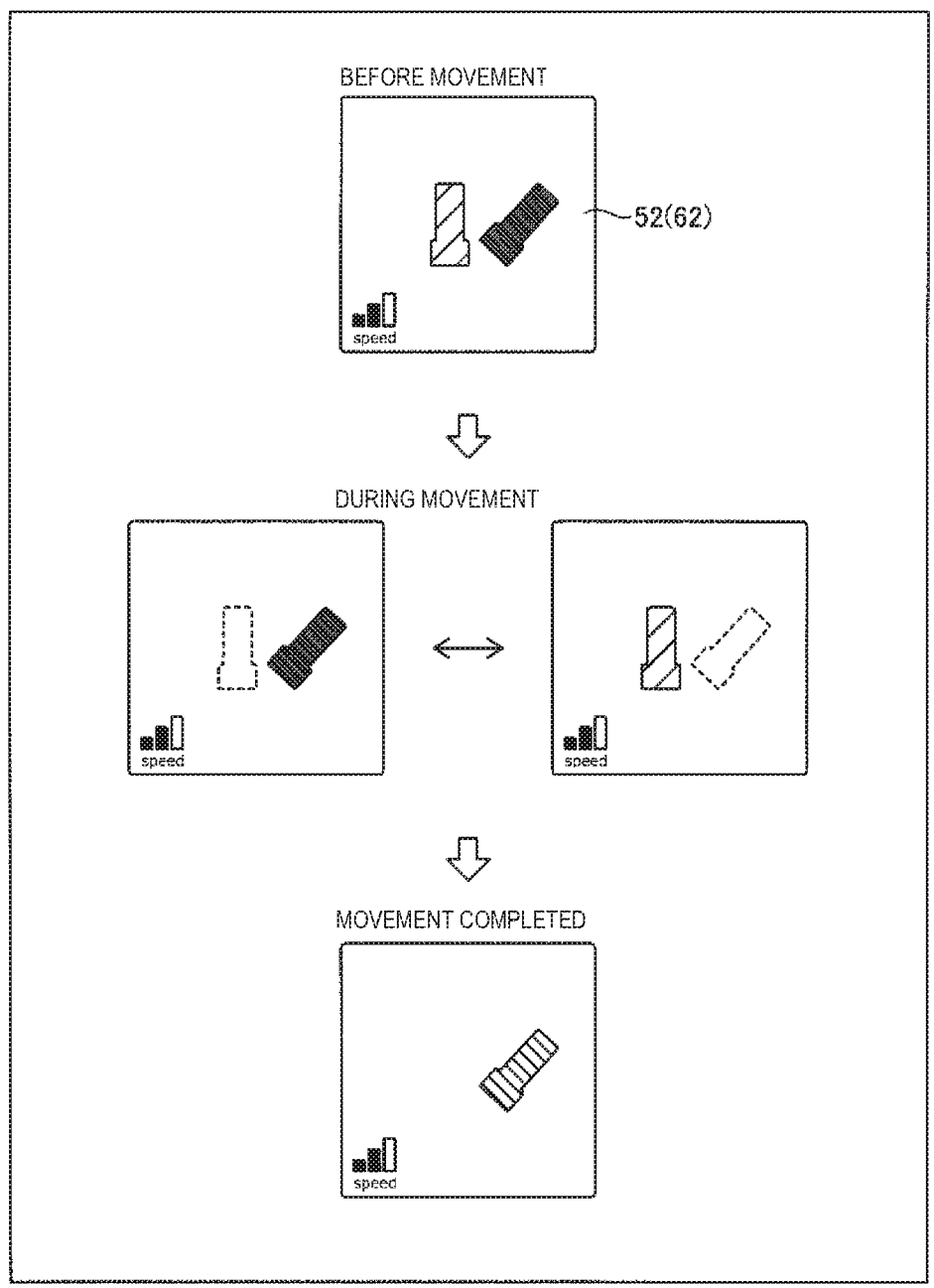
FIG. 8 is a diagram illustrating an example of a display of the robotic operating table according to one or more embodiments.

In one or more embodiments, as illustrated in FIG. 8, while the move operation unit 53 (63) is receiving a move operation to move the table 1, the operation controller 51 (61) controls the display 52 (62) to display the position of the table 1 before movement and the position of the table 1 after the movement in a distinguishable manner. Specifically, while the move operation unit 53 (63) is receiving a move operation to move the table 1, the operation controller 51 (61) controls the display 52 (62) to display diagrams (illustrations) representing the table 1 such that the position before the movement and the position after the movement can be distinguished from each other. The position after movement is a preset position fixed as a position after movement in advance.

The controller 3 controls drive of the robotic arm 2 to move the table 1 while the trigger unit 54 (64) and the move operation unit 53 (63) are operated together. Meanwhile, when the table 1 arrives at the preset position, i.e., the position after the movement, the controller 3 performs control that invalidates the operation of the move operation unit 53 (63) and stops the movement of the table 1. Then, when a user stops the operation of the trigger unit 54 (64), the controller 3 performs control that stops energization of the motor 41 and actuates the electromagnetic brake 43. In this way, the table 1 and the robotic arm 2 are fixed at the preset position immediately. The controller 3 may notify the user of the arrival at the preset position.

In one or more embodiments, while the move operation unit 53 (63) is receiving a move operation to move the table 1, the operation controller 51 (61) may control the display 52 (62) to display the position of the table 1 before movement and the position of the table 1 after the movement in colors different from each other and display the position after the movement in a flashing manner. While the move operation unit 53 (63) is receiving a move operation to move the table 1, the operation controller 51 (61) controls the display 52 (62) to display the position of the table 1 after the movement in a flashing manner alternately in colors different from each other.

While the move operation unit 53 (63) is receiving a move operation to move the table 1, the operation controller 51 (61) controls the display 52 (62) to alternately display the position of the table 1 before movement and the position of the table 1 after the movement. When movement of the table 1 is completed, the operation controller 51 (61) controls the display 52 (62) to display the position after the movement without displaying the position before the movement. Specifically, when the table 1 is moved to a target position and the electromagnetic brake 43 of the joint driver 4 of the robotic arm 2 is turned on, the display 52 (62) stops displaying the position before the movement. Thus, before the movement of the table 1, the display 52 (62) displays both of the position before the movement and the position after the movement in colors different from each other. Then, during the movement of the table 1, the display 52 (62) displays the position before the movement and the position after the movement in an alternately flashing manner. When the movement of the table 1 is completed, the display 52 (62) displays only the position after the movement, which is the current position. The color of the displayed position of the table 1 is changed from the color of a position after movement to the color of a current position.

The operation controller 51 (61) controls the display 52 (62) to provide different displays of the respective operation modes. Specifically, the operation controller 51 (61) controls the display 52 (62) to display an image in accordance with an operation mode set by the operation mode setting unit 55 (65).

The operation controller 51 changes the moving speed of the table 1 in accordance with a tilt at which the joystick 53a is operated. Specifically, the operation controller 51 sets a lower moving speed for a smaller tilt of the joystick 53a and sets a higher moving speed for a larger tilt of the joystick 53a. The operation controller 61 changes the moving speed of the table 1 in accordance with an operation of the moving speed switching button 67.

(Configuration of Radiographic Imaging Apparatus)

The following describes the configuration of the radiographic imaging apparatus 300 with reference to FIG. 1.

As illustrated in FIG. 1, the radiographic imaging apparatus 300 is capable of capturing a radiographic projection image of the patient 10 being placed on the table 1. The X-ray irradiation unit 301 and the X-ray detection unit 302 are supported by the C-arm 303. The X-ray irradiation unit 301 and the X-ray detection unit 302 are moved along with movement of the C-arm 303 and disposed facing to each other on both sides of the patient 10 at the imaging position at radiographic imaging. For example, one of the X-ray irradiation unit 301 and the X-ray detection unit 302 is disposed in a space above the table 1, and the other is disposed in a space below the table 1. At radiographic imaging, the C-arm 303 supporting the X-ray irradiation unit 301 and the X-ray detection unit 302 is disposed in the spaces above and below the table 1.

The X-ray irradiation unit 301 is disposed facing to the X-ray detection unit 302. The X-ray irradiation unit 301 is capable of emitting X-ray toward the X-ray detection unit 302. The X-ray detection unit 302 detects the X-ray emitted by the X-ray irradiation unit 301. The X-ray detection unit 302 includes a flat panel detector (FPD). The X-ray detection unit 302 captures a radiographic image based on detected X-ray. Specifically, the X-ray detection unit 302 converts detected X-ray into an electric signal and transmits the electric signal to an image processing unit (not illustrated).

The C-arm 303 has one end connected with the X-ray irradiation unit 301 and the opposite end connected with the X-ray detection unit 302. The C-arm 303 has a substantially C shape. With this configuration, at radiographic imaging, the C-arm 303 can support the X-ray irradiation unit 301 and the X-ray detection unit 302 while extending around the table 1 and the patient 10 to avoid interference therewith. The C-arm 303 is movable relative to the table 1. Specifically, the C-arm 303 is movable in the horizontal direction and the vertical direction to dispose the X-ray irradiation unit 301 and the X-ray detection unit 302 at desired positions relative to the patient 10 being placed on the table 1, and is also rotatable about a rotation axis extending in the horizontal direction and a rotation axis extending in the vertical direction. The C-arm 303 is moved by a drive unit (not illustrated) based on an operation by a medical person (operator). The C-arm 303 is manually movable by a medical person (operator). The display 400 is capable of displaying a radiographic fluoroscopic image captured by the radiographic imaging apparatus 300, and a radiographic image captured by the radiographic imaging apparatus 300.

(Effects of Embodiments)

According to one or more embodiments, effects as described below can be obtained.

As described above, one or more embodiments may include the controller 3 that controls, while the move operation unit 53 or 63 is receiving a move operation to move the table 1, the light emitters 120 to emit light. With this configuration, even when the table 1 is moved at low speed to reduce a burden on the patient 10 being placed, a medical person such as a surgeon, an assistant, a nurse, or a medical technician can easily recognize that the table 1 is moving through light emission by the light emitters 120. One or more embodiments may also include the robotic arm 2 including one end supported on the base 21 and the opposite end supporting the table 1. With this configuration, the table 1 can be moved by the robotic arm 2, and thus the movement range and freedom of the table 1 can be increased as compared to a case where the table 1 is moved by a base fixed to the floor. Accordingly, the movement range and freedom of the table 1 on which to place the patient 10 can be increased, and the medical person can easily recognize that the table 1 is moving. When the move operation unit 53 or 63 is unintentionally operated, light emission from the light emitters 120 may prevent the operation device 5 or 6 from being operated mistakenly.

In one or more embodiments, as described above, while the move operation unit 53 or 63 is receiving a move operation to move the table 1, the controller 3 may control the sound generation unit 122 to generate notification sound. With this configuration, since it is notified that the table 1 is moving by the notification sound from the sound generation unit 122 in addition to the light emission from the light emitters 120, a medical person can more reliably recognize that the table 1 is moving. When the move operation unit 53 or 63 is unintentionally operated, the light emission from the light emitters 120 and the notification sound emission from the sound generation unit 122 may effectively prevent the operation device 5 or 6 from being operated mistakenly.

In one or more embodiments, as described above, the light emitters 120 may be provided on the side parts on both sides of the table 1 in the transverse direction (Y direction). With this configuration, the light emitters 120 can be easily visually recognized from both sides, i.e., one and the other sides of the table 1 in the transverse direction, and thus it is possible to easily recognize, from either side of the table 1 in the transverse direction, that the table 1 is moving.

In one or more embodiments, as described above, the light emitters 120 may be provided near one end of the table 1 in the longitudinal direction (X direction). With this configuration, the light emitters 120, which are disposed near the one end of the table 1 in the longitudinal direction, are unlikely to be covered by a surgical cover on the patient 10 placed on the table 1. Accordingly, when the patient 10 is placed and covered by a surgical cover, a medical person can easily recognize that the table 1 is moving.

In one or more embodiments, as described above, the table 1 may include the table body 11 made of a radiolucent material and the support unit 12 supporting the table body 11, the opposite end of the robotic arm 2 supports the support unit 12 near one end of the table 1, and the light emitters 120 are disposed on the support unit 12. With this configuration, when the robotic arm 2 is disposed close to the support unit 12 to provide a sufficient space below the table body 11, the radiographic imaging apparatus 300 can be placed below the table body 11 to perform radiographic imaging on the patient 10 being placed on the table 1. Since the light emitters 120 are provided at the support unit 12, the light emitters 120 are unlikely to be covered by a surgical cover on the patient 10 placed on the table body 11, unlike a case where the light emitters 120 are provided at the table body 11. Accordingly, when the patient 10 is placed and covered by a surgical cover, a medical person can easily recognize that the table 1 is moving.

In one or more embodiments, as described above, each light emitter 120 may include the light sources 121, and while the move operation unit 53 or 63 is receiving a move operation to move the table 1 in a predetermined direction, the controller 3 controls the light sources 121 to sequentially emit light to indicate that the table 1 is moving to the predetermined direction. With this configuration, light emission from the light sources 121 enables easy recognition of the moving direction.

In one or more embodiments, as described above, the controller 3 may control drive of the robotic arm 2 to move the table 1 while at least one of the directional operation units 63a is operated. With this configuration, the table 1 is moved only while the move direction units 63a is operated, and thus only the operation of the move direction units 63a just has to be stopped to stop movement of the table 1. Accordingly, the movement of the table 1 can be stopped reliably and immediately.

In one or more embodiments, as described above, the controller 3 may control drive of the robotic arm 2 to move the table 1 while the joystick 53a is operated. With this configuration, the table 1 is moved only while the joystick 53a is operated, and thus only the operation of the joystick 53a just has to be stopped to stop movement of the table 1. Accordingly, the movement of the table 1 can be stopped reliably and immediately.

In one or more embodiments, as described above, the controller 3 may control drive of the robotic arm 2 to move the table 1 while the trigger unit 54 (64) and the move operation unit 53 (63) are operated together. Specifically, when the trigger unit 54 (64) is operated, the motor 41 is energized and braking of the motor 41 by the electromagnetic brake 43 is released. As a result, the operation of the move operation unit 53 (63) is enabled, so that the table 1 can be moved only while the trigger unit 54 (64) is operated. With this configuration, when the move operation unit 53 (63) is unintentionally operated, the table 1 is not moved unless the trigger unit 54 (64) is operated. Accordingly, unintentional movement of the table 1 can be effectively prevented.

In one or more embodiments, as described above, the robotic arm 2 may include one end supported on the base 21 to be rotatable about an axis extending in the vertical direction (Z direction) and the opposite end supporting the vicinity of one end of the table 1 in the longitudinal direction (X direction), and has at least six degrees of freedom to move the table 1. With this configuration, the table 1 can be easily moved to a desired position by the robotic arm 2 having at least six degrees of freedom. In addition, the movement range and freedom of the table 1 on which to place the patient 10 can be effectively increased by the robotic arm 2 having at least six degrees of freedom.

As described above, one or more embodiments may include the operation controller 51 (61) that controls, while the move operation unit 53 or 63 is receiving a move operation to move the table 1, the displays 52 and 62 to display the position of the table 1 before movement and the position of the table 1 after the movement in a distinguishable manner. With this configuration, a medical person can easily recognize that the table 1 is moving by referring to the display on the displays 52 and 62, and can easily recognize the position of the table 1 before the movement and the position of the table 1 after the movement.

In one or more embodiments, as described above, while the move operation unit 53 (63) is receiving a move operation to move the table 1, the operation controller 51 (61) controls the displays 52 and 62 to display diagrams (illustrations) representing the table 1, and the position of the table 1 before movement and the position of the table 1 after the movement in a distinguishable manner. With this configuration, the displays 52 and 62 display the diagrams representing the table 1 such that the position before the movement and the position after the movement can be distinguished from each other, and thus the movement of the table 1 can be easily checked by referring to the diagrams.

In one or more embodiments, as described above, while the move operation unit 53 (63) is receiving a move operation to move the table 1, the operation controller 51 (61) may control the displays 52 and 62 to display the position of the table 1 before movement and the position of the table 1 after the movement in colors different from each other and display the position after the movement in a flashing manner. With this configuration, since the position of the table 1 before the movement and the position of the table 1 after the movement are displayed in colors different from each other and the position after the movement is displayed in a flashing manner, the position of the table 1 before the movement and the position thereof after the movement can be easily distinguished.

In one or more embodiments, as described above, while the move operation unit 53 (63) is receiving a move operation to move the table 1, the operation controller 51 (61) may control the displays 52 and 62 to display the position of the table 1 after the movement in a flashing manner alternately in colors different from each other. With this configuration, since the position of the table 1 after the movement is displayed in a flashing manner in colors different from each other, the position of the table 1 after the movement can be easily recognized.

In one or more embodiments, as described above, while the move operation unit 53 (63) is receiving a move operation to move the table 1, the operation controller 51 (61) may control the displays 52 and 62 to alternately display the position of the table 1 before movement and the position of the table 1 after the movement. With this configuration, since the position of the table 1 before movement and the position of the table 1 after the movement are alternately displayed, the position of the table 1 before the movement and the position thereof after the movement can be easily distinguished.

In one or more embodiments, as described above, the operation controller 51 (61) may control the displays 52 and 62 to display the position of the table 1 after the movement without displaying the position of the table 1 before the movement when movement of the table 1 is completed. With this configuration, since only the position of the table 1 after the movement is displayed after the movement is completed, the completion of the movement can be easily recognized. In addition, display on the displays 52 and 62 after the completion of the movement can be simplified.

In one or more embodiments, as described above, the operation controller 51 (61) may control the displays 52 and 62 to provide the different displays of the respective operation modes. With this configuration, the table 1 can be easily moved through selection of an operation mode by the operation mode setting unit 55 (65).

In one or more embodiments, as described above, the operation modes may include the yaw mode in which the table 1 is rotated about a rotation axis extending in the vertical direction (Z direction) in a horizontal plane, the horizontal movement mode in which the table 1 is linearly moved in a horizontal plane, the vertical movement mode in which the table 1 is vertically moved, the roll mode in which the table 1 is rotated about an axis parallel to the longitudinal direction (X direction) of the table 1, and the pitch mode in which the table 1 is rotated about an axis parallel to the transverse direction (Y direction) of the table 1. This configuration enables effective increase in the degrees of freedom of movement of the table 1.

In one or more embodiments, as described above, the operation mode setting unit 55 (65) and the move operation unit 53 (63) may have background colors different from each other. This configuration may prevent a user from mistakenly operating the operation mode setting unit 55 (65) in place of the move operation unit 53 (63) or vice versa, thereby effectively preventing mistakes in operations.

In one or more embodiments, as described above, the operation device 6 includes the moving speed switching button 67 for changing the moving speed of the table 1. With this configuration, the moving speed of the table 1 can be easily changed by the moving speed switching button 67. Since the moving speed of the table 1 is changeable, the moving speed can be decreased to reduce a burden on the patient 10 when the patient 10 is placed on the table 1, and the moving speed can be increased to move the table 1 fast when the patient 10 is not placed on the table 1.

In one or more embodiments, as described above, the operation controller 51 may change the moving speed of the table 1 in accordance with a tilt at which the joystick 53a is operated. With this configuration, the moving speed of the table 1 can be easily changed by changing the tilt of the joystick 53a.

(Modifications)

The embodiments disclosed herein should be considered exemplary in all aspects, non-exhaustive and not limiting. The scope of the present invention is indicated by the claims rather than the explanation of the above embodiments and also embraces all changes that come within the meaning and range of equivalents of the claims.

For example, in one or more embodiments, a hybrid operation system may include a radiographic imaging apparatus. Additional or alternative embodiments may not be limited to such examples. For example, the hybrid operation system may include a magnetic resonance imaging apparatus that captures a magnetic resonance image of a patient. Alternatively, the hybrid operation system may include both of a radiographic imaging apparatus and a magnetic resonance imaging apparatus.

In one or more embodiments, the robotic operating table may be provided with two operation devices. Additional or alternative may not be limited to such examples. For example, the robotic operating table may be provided with one operation device or may be provided with three operation devices or more.

In one or more embodiments, an operation device may be connected with a controller through wired communication. Additional or alternative may not be limited to such examples. For example, the operation device may be connected with the controller through wireless communication.

In the above-described embodiments, a sound generation unit is provided to the table. Additional or alternative may not be limited to such examples. For example, the sound generation unit may be provided to an operation device or a robotic arm. Alternatively, the sound generation unit may be provided separately from the table, the operation device, and the articulated robotic arm.

In the above-described embodiments, a light emitter includes light sources. Additional or alternative may not be limited to such examples. For example, the light emitter may include a single light source.

Figure 9:
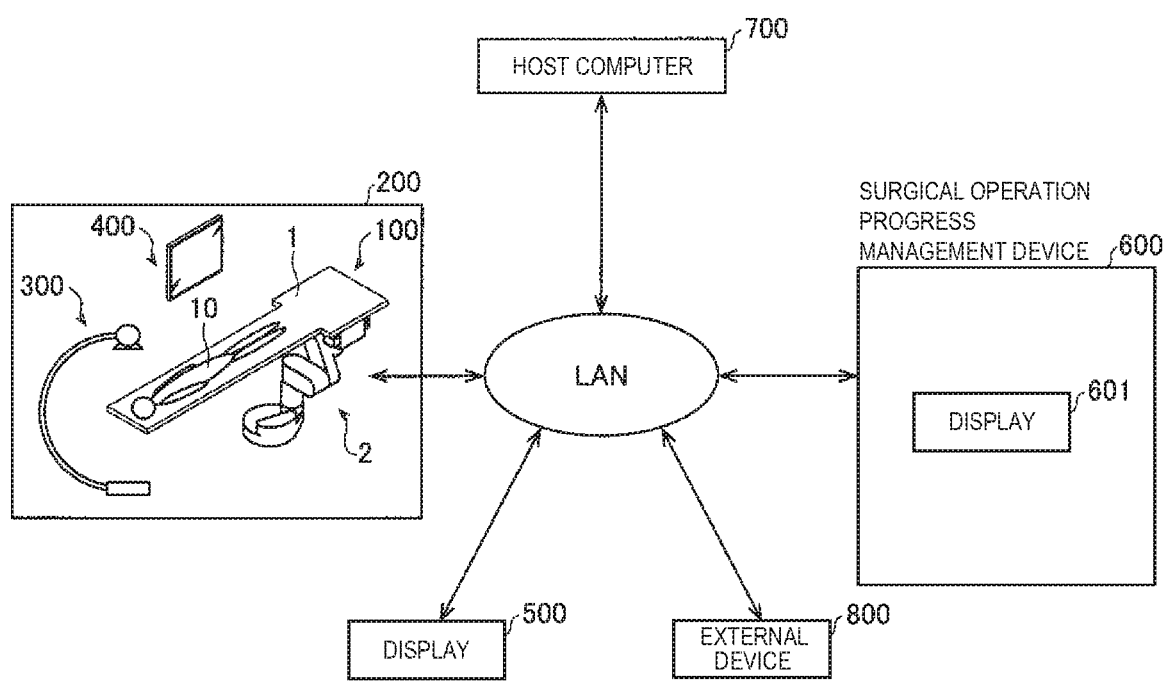
FIG. 9 is a diagram illustrating an example of a display according to one or more modification of embodiments.

In one or more embodiments, a display may be provided to an operation device. Additional or alternative may not be limited to such examples. For example, the display that displays a status of a table may be provided separately from the operation device. In a modification illustrated in FIG. 9, a display provided outside an operation room may display, for example, the state of a table, the state of an operation of an operation device, and an operation screen. Specifically, as illustrated in FIG. 9, the state of the table and the like may be displayed on a display 500 provided outside the hybrid operation room 200 and connected with a local area network (LAN) inside a hospital in which the hybrid operation room 200 is provided. The display 500 is provided at, for example, a nurse station. When a surgical operation progress management device 600 for managing the progress of a surgical operation is provided outside of the hybrid operation room 200, the state of the table and the like may be displayed on a display 601 of the surgical operation progress management device 600. The display 601 of the surgical operation progress management device 600 is provided at, for example, a control center adjacent to the hybrid operation room 200. For example, a host computer 700 and an external device 800 such as a portable terminal owned by hospital staff may be connected with the LAN inside the hospital.

In one or more embodiments, an operation mode setting unit and a move operation unit may have background colors different from each other. Additional or alternative may not be limited to such examples. For example, the operation mode setting unit and the move operation unit may provide touch feelings different from each other. For example, the surfaces of the operation mode setting unit and the move operation unit may have uneven shapes different from each other.

In one or more embodiments, a horizontal articulated assembly may include three horizontal joints. Additional or alternative may not be limited to such examples. For example, the horizontal articulated assembly may include two horizontal joints or may include four horizontal joints or more.

In one or more embodiments, a vertical articulated assembly may include three vertical joints. Additional or alternative may not be limited to such examples. For example, the vertical articulated assembly may include two vertical joints or may include four vertical joints or more.

In one or more embodiments, an articulated robotic arm may include three horizontal joints in a series and three vertical joints in a series. Additional or alternative may not be limited to such examples. For example, the articulated robotic arm may be a vertical articulated robot including parts at which rotation axes of joints adjacent to each other are orthogonal to each other.

In one or more embodiments, the articulated robotic arm may have the seven degrees of freedom. Additional or alternative may not be limited to such examples. For example, the articulated robotic arm may have six or less degrees of freedom or eight or more degrees of freedom, but preferably, may have at least six degrees of freedom.

In one or more embodiments, a base may be buried and fixed in the floor. Additional or alternative may not be limited to such examples. For example, the base may be fixed on the floor.

In one or more embodiments, the controller 3 may be disposed in the base 21. Additional or alternative may not be limited to such examples. For example, the controller 3 may be housed in a control box, and the control box may be disposed at an optional position inside the hybrid operation room 200 or the control center adjacent to the hybrid operation room 200.

In one or more embodiments, the controller 3 may perform control to stop movement of the table 1 by invalidating the operation of the move operation unit 53 (63) when the table 1 arrives at a preset position, and to stop energization of the motor 41 and actuate the electromagnetic brake 43 when the operation of the trigger unit 54 (64) is stopped by a user. Additional or alternative may not be limited to such examples. For example, when the table 1 arrives at a preset position, the controller 3 may stop energization of the motor 41 and actuate the electromagnetic brake 43 even though the move operation unit 53 (63) and the trigger unit 54 (64) are operated together.

In the case of such a conventional operating table as disclosed in Japanese Patent Application Publication No. 2014-100301, the table can move horizontally within only a small range with poor freedom of movement. Thus, it is difficult to move the table to various positions (such as a patient receiving position, an anesthetization position, a surgical operation position, and an imaging position) by increasing the movement range and freedom of the table. In addition, in the case of such an operating table, the small movement range of the operating table makes it difficult to leave sufficient spaces around the positions at which medical persons such as surgeons, assistants, nurses, and medical technicians stand, and therefore makes it difficult for them to perform a surgical operation. Moreover, when a medical person is about to move the table, it is difficult for the medical person to easily recognize that the table is moving.

One or more embodiments may provide a robotic operating table, a hybrid operation room, and a robotic operating table operation device which achieve increases in the movement range and freedom of a patient placement table and which enable a medical person to easily recognize that the table is moving.

The above-described aspects may be combined with each other as practicable within the contemplated scope of embodiments. The above described embodiments are to be considered in all respects as illustrative, and not restrictive. The illustrated and described embodiments may be extended to encompass other embodiments in addition to those specifically described above without departing from the intended scope of the invention. The scope of the invention is to be determined by the appended claims when read in light of the specification including equivalents, rather than solely by the foregoing description. Thus, all configurations including configurations that fall within equivalent arrangements of the claims are intended to be embraced in the invention.

What is claimed is:
1. A robotic operating table comprising:
a patient placement table;

a robotic arm comprising a plurality of joints, and having a first end supported on a base and a second end supporting the patient placement table;
a display; and
an operation device including a move operation unit that comprises an input device to be operated by a user and receives, from the input device, a move operation to move the patient placement table,
wherein the display displays both a first image indicating the patient placement table in a first position before movement and a second image indicating the patient placement table in a second position after the movement, the first image and the second image displayed in one screen in a distinguishable manner while the move operation unit is receiving the move operation to move the patient placement table.

2. The operating table according to claim 1, wherein each of the joints includes a motor and an electromagnetic brake, and
when the patient placement table is disposed at a position after the movement, the robotic arm fixes the posture of the robotic arm by stopping energization of the motor and actuating the electromagnetic brake.

3. A robotic operating table operation device comprising:
a display; and
a move operation unit that comprises an input device to be operated by a user and receives, from the input device, a move operation to move a patient placement table of the robotic operating table,
wherein the operating table includes the patient placement table, and a robotic arm comprising a plurality of joints, and having a first end supported on a base and a second end supporting the patient placement table, and
wherein, while the move operation unit is receiving the move operation to move the patient placement table, the display displays both a first image indicating the patient placement table in a first position before movement and a second image indicating the patient placement table in a second position after the movement, the first image and the second image displayed in one screen in a distinguishable manner.

4. The operation device according to claim 3, wherein, while the move operation unit is receiving the move operation to move the patient placement table, the display displays, as the first image, a first diagram representing the patient placement table before the movement and, as the second image, a second diagram representing the patient placement table after the movement.

5. The operation device according to claim 3, wherein, while the move operation unit is receiving the move operation to move the patient placement table, the display displays the first image and the second image in colors different from each other and display the second image in a flashing manner.

6. The operation device according to claim 3, wherein, while the move operation unit is receiving the move operation to move the patient placement table, the display displays the first image and the second image in a flashing manner alternately in colors different from each other.

7. The operation device according to claim 3, wherein, while the move operation unit is receiving the move operation to move the patient placement table, the display alternately displays the first image and the second image.

8. The operation device according to claim 3, wherein, when the movement of the patient placement table is completed, the display displays the second image without displaying the first image.

9. The operation device according to claim 3, further comprising an operation mode setting unit that comprises a second input device to be operated by the user and sets one of operation modes, wherein
the display provides different displays of the respective operation modes.

10. The operation device according to claim 9, wherein the operation modes include a yaw mode in which the patient placement table is rotated in a horizontal plane about a rotation axis in a vertical direction, a horizontal movement mode in which the patient placement table is linearly moved in the horizontal plane, a vertical movement mode in which the patient placement table is vertically moved, a roll mode in which the patient placement table is rotated about an axis parallel to a longitudinal direction of the patient placement table, and a pitch mode in which the patient placement table is rotated about an axis parallel to a transverse direction of the patient placement table.

11. The operation device according to claim 9, wherein the operation mode setting unit and the move operation unit have background colors different from each other.

12. The operation device according to claim 9, further comprising a moving speed switching button that changes a moving speed of the patient placement table.

13. The operation device according to claim 9, wherein the move operation unit includes a joystick, and
the robotic arm changes a moving speed of the patient placement table in accordance with a tilt at which the joystick is operated.

14. The operation device according to claim 9, wherein each of the joints includes a motor and an electromagnetic brake, and
when the patient placement table is disposed at a position after the movement, the robotic arm fixes the posture of the robotic arm by stopping energization of the motor and actuating the electromagnetic brake.

15. A robotic operating table operation device comprising:
a display; and
a move operation unit that comprises an input device to be operated by a user and receives, from the input device, a move operation to move a patient placement table of the robotic operating table,
wherein the operating table includes the patient placement table, and a robotic arm comprising a plurality of joints, and having a first end supported on a base and a second end supporting the patient placement table, and
wherein, while the move operation unit is receiving the move operation to move the patient placement table, the display displays a first image indicating the patient placement table in a first position before movement and a second image indicating the patient placement table in a second position after the movement at the same time.

16. The operation device according to claim 15, wherein, while the move operation unit is receiving the move operation to move the patient placement table, the display displays, as the first image, a first diagram representing the patient placement table before the movement and, as the second image, a second diagram representing the patient placement table after the movement.

17. The operation device according to claim 15, wherein, while the move operation unit is receiving the move operation to move the patient placement table, the display displays the first image and the second image in colors different from each other.

18. The operation device according to claim 15, wherein, while the move operation unit is receiving the move operation to move the patient placement table, the display displays the first image and the second image in colors different from each other and display the second image in a flashing manner.

19. The operation device according to claim 15, wherein, while the move operation unit is receiving the move operation to move the patient placement table, the display alternately displays the first image and the second image.

* * * * *